United States Patent [19]

Zhagars et al.

[11] Patent Number: 4,610,767

[45] Date of Patent: Sep. 9, 1986

[54] PHOTOCHEMICAL METHOD FOR PREPARING 4-KETO-9-METHYLPHENAZINE

[75] Inventors: Andrei K. Zhagars; Voldemar Y. Grinshtein; Nikolai B. Novak, all of Riga, U.S.S.R.

[73] Assignee: Latviisky Gosudarstvenny Universitet Imeni P.Stuchki, Riga, U.S.S.R.

[21] Appl. No.: 731,838

[22] Filed: May 8, 1985

[51] Int. Cl.[4] ............................................. B01J 19/12
[52] U.S. Cl. ................................................ 204/157.81
[58] Field of Search ................................... 204/157.81

[56] References Cited

U.S. PATENT DOCUMENTS 3,196,097  7/1965  Ide et al. ...................... 204/157.81

Primary Examiner—Howard S. Williams
Attorney, Agent, or Firm—Burgess, Ryan & Wayne

[57] ABSTRACT

A method for preparing 4-keto-9-methylphenazine, which comprises methylation of phenazine with dimethylsulphate, followed by keeping the resulting reaction mixture at a temperature within the range of from 0° to 10° C. and carrying out a photo-chemical oxidation of the resulting 9-methylphenazinium methylsulphate by UV-irradiation for not longer than 3 hours, bringing the pH of the reaction mixture to 8.5-9.5, a repeated irradiation thereof for additional 3-5 hours, and isolation of the desired product.

2 Claims, No Drawings

PHOTOCHEMICAL METHOD FOR PREPARING 4-KETO-9-METHYLPHENAZINE

FIELD OF APPLICATION

The present invention relates to organic chemistry and, more particularly, it relates to a method for preparing 4-keto-9-methylphenazine useful in medicine as an antiseptic and for the synthesis of pharmaceutical compounds.

PRIOR ART

Known in the art is a method for preparing 4-keto-9-methylphenazine from phenazine subjected to interaction with dimethylsulphate in nitrobenzene upon heating for 7 minutes, whereafter the reaction mixture is cooled with ice, the resulting 9-methylphenazinium methylsulphate is dissolved in water and allowed to stand in an open vessel in sunlight, followed by the addition of a 10% solution of sodium carbonate and the desired product (4-keto-9-methylphenazine) is extracted with the yield of 16.45% as calculated for the starting phenazine. (Ilwein H. M. The Phenazine Series. Part VI. Reactions of Alkyl Phenazonium Salts, the Phenazyls.-J. Chem. Soc., 1937, p. 1704–1711).

The prior art methods feature but low yields of the desired product (not more than 35% as calculated for 9-methylphenazinium methylsulphate) due to insufficient methylation of phenazine with dimethylsulphate for 7 minutes at the temperature of 100° C. Elevation of the methylation temperature or extension of the reaction time results in resinification. A disadvantage of the photochemical oxidation of 9-methylphenazinium methylsulphate is a long time of its irradiation depending on weather conditions, whereby the yield of the desired product is lowered due to instability of 9-methylphenazinium methylsulphate and its liability to demethylation. Furthermore, the ions of methylsulphate formed during the irradiation react with the starting 9-methylphenazinium methylsulphate and cause an intensive demethylation of the latter.

BRIEF DESCRIPTION OF THE INVENTION

It is the main object of the present invention to increase the desired product yield.

It is another object of the invention to simplify the process of preparing the desired product.

The main and other objects of the present invention are accomplished by that in the method for preparing 4-keto-9-methylphenazine by methylation of phenazine with dimethylsulphate, followed by a photochemical oxidation of the resulting 9-methylphenazinium methylsulphate and isolation of the desired product, according to the present invention. After treatment of phenazine with dimethylsulphate the reaction mixture is kept at a temperature within the range of from 0° to 10° C., whereafter a photochemical oxidation of the resulting 9-methylphenazinium methylsulphate by UV-radiation is conducted for not longer than 3 hours and then the pH of the reaction medium is brought to 8.5–9.5 and irradiation is conducted for additional 3–5 hours, whereafter the desired product is isolated.

In order to increase the desired product yield, it is advisable that the reaction mixture after methylation of phenazine be allowed to stand for a period of 40 to 50 hours.

The method according to the present invention makes it possible to increase the desired product yield to 65% as calculated for 9-methylphenazinium methylsulphate (as against 35% in the prior art method) and to simplify the process.

DETAILED DESCRIPTION OF THE INVENTION

The method according to the present invention is effected in the following manner. Phenazine is treated with dimethylsulphate, then the reaction mixture is allowed to stand for preferably 40 to 50 hours at a temperature within the range of from 0° to 10° C. During this time the reaction of methylation is completed, but no resinification or decomposition of the formed 9-methylphenazinium methylsulphate occur. The yield is increased from 35 to 67% as calculated for the starting phenazine. The photochemical oxidation of 9-methylphenazinium methylsulphate is carried out in a closed quartz flask by irradiating it from a UV-radiation source (e.g., with the power of 1.5 kW from the distance of 30–40 cm), whereafter a 0.1M solution of sodium carbonate is added (or another alkali) to a pH of 8.5–9.5. The liberated methylsulphate gets combined. The irradiation lasts for additional 3–5 hours, the solution is again alkalized with a 10% solution of sodium carbonate or another alkali, and the desired product is isolated by extraction. The yield of the thus-prepared 4-keto-9-methylphenazine is 61% as calculated for 9-methylphenazinium methylsulphate or 40.1% as calculated for phenazine.

An advantage of the method according to the present invention over the prior art resides in that by means of lead carrying out of a complete methylation of phenazine increases the yield of 9-methylphenazinium methylsulphate from 35 to 67%. The synthesis of 4-keto-9-methylphenazine can be conducted not-withstanding the weather conditions and the effect of the atmosphere is eliminated (whereas in the prior art method it is conducted in daylight). The fact that the methylsulphate-ion gets combined ensures a yield of 4-keto-9-methylphenazine as high as 65%.

For a better understanding of the present invention the following examples are given hereinbelow by way of illustration.

EXAMPLE 1

1.76 g (0.011 mol) of phenazine and 33.5 ml of dry nitrobenzene are heated to boiling, cooled to 100° C., added with 12.2 g (0.011 mol) of freshly distilled dimethylsulphate and heated for 7 minutes at the temperature of 100° C. Then the reaction mixture is cooled with ice and allowed to stand for 48 hours at the temperature of 4° C. in a refrigerator. The formed precipitate is filtered off, washed with 30 ml of ethyl ether and recrystallized from 15 ml of ethanol. 2.0 g of 9-methylphenazinium methylsulphate (67%) are thus obtained in the form of yellowish crystals melting at 155°–157° C.

Found, %: C 55.03; H 4.80; N 9.25; $C_{14}H_{14}N_2O_4$. Calculated, %: C 54.89; H 4.61; N 9.14.

2 g (0.011 mol) of 9-methylphenazinium methylsulphate are dissolved in 2 l of distilled water and then exposed for 24 hours to UV-radiation (from a source having a power 1.5 kW, at a distance of 30–40 cm) at the temperature of 40° C. in a closed quartz flask, then added with a 0.1M solution of sodium carbonate to the pH of 9.0. Then the irradiation is continued for additional 4 hours. The solution is filtered, added with 40 ml of a 10% solution of sodium carbonate and extracted four times with 200 ml portions of chloroform. The extracts are combined, dried with potassium carbonate and evaporated to the volume of 70 ml, then 250 ml of hot hexane are added and the mixture is cooled. The formed precipitate is filtered off, washed with 200 ml of hexane, recrystallized from 50 ml of water to give 0.83 g of 4-keto-9-methylphenazine (61%) in the form of blue crystals melting at 133°–135° C.

Found, %: C 74.21; H 4.80; N 13.01. $C_{13}H_{10}N_2O$. Calculated, %: C 74.30; H 4.76; N 13.32.

EXAMPLE 2

9-Methylphenazinium methylsulphate is obtained as described in Example 1, except that the mixture after methylation is allowed to stand for 40 hours at the temperature of 0° C. to give 1.9 g of 9-methylphenazinium methylsulphate (60%) in the form of yellowish crystals with the melting point of 155°–157° C.

Further steps of the process are conducted as described in Example 1 hereinbefore. The solution of 9-methylphenazinium methylsulphate in distilled water is first irradiated for 3 hours and the reaction mixture is brought to the pH of 8.5 by using a 0.1N solution of sodium hydroxide, whereafter the irradiation is continued for additional 5 hours to give 0.79 g (58%) of 4-keto-9-methylphenazine in the form of blue crystals with the melting point of 133°–135° C.

EXAMPLE 3

In a manner similar to that described in Example 1 9-methylphenazinium methylsulphate is obtained, the only exception is that the reaction mixture after methylation is kept at the temperature of 10° C. for 5 hours to give 1.3 g (43.55%) of yellowish crystals of 9-methylphenazinium sulphate melting at 155°–157° C.

Then the process is conducted as described in Example 1, except for the fact that the preliminary irradiation is carried out for one hour, pH of the solution is brought to 9.5 by means of a 0.1N solution of potassium hydroxide and the irradiation is continued for additional 3 hours to give 0.43 g (47%) of blue crystals of 4-keto-9-methylphenazine having a m.p. of 134°–135° C.

What we claim is:

1. A method for preparing 4-keto-9-methylphenazine, comprising methylation of phenazine with dimethylsulphate, followed by keeping the reaction mixture at a temperature within the range of from 0° to 10° C. and conducting a photochemical oxidation of the resulting 9-methylphenazinium methylsulphate by UV-radiation for not longer than 3 hours, bringing the pH of the reaction medium to 8.5–9.5, a repeated irradiation thereof for 3–5 hours, and isolation of the desired product.

2. A method according to claim 1, wherein, to ensure a higher yield of the desired product, the reaction mixture after treatment of phenazine with dimethylsulphates is allowed to stand for a period of 40 to 50 hours.

* * * * *